(12) United States Patent
Taniguchi et al.

(10) Patent No.: US 9,019,492 B2
(45) Date of Patent: Apr. 28, 2015

(54) DEFECT INSPECTION DEVICE AND DEFECT INSPECTION METHOD

(75) Inventors: Atsushi Taniguchi, Fujisawa (JP); Taketo Ueno, Kawasaki (JP); Shunichi Matsumoto, Hitachinaka (JP); Toshifumi Honda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 179 days.

(21) Appl. No.: 13/989,835

(22) PCT Filed: Nov. 10, 2011

(86) PCT No.: PCT/JP2011/076013
§ 371 (c)(1),
(2), (4) Date: May 28, 2013

(87) PCT Pub. No.: WO2012/073673
PCT Pub. Date: Jun. 7, 2012

(65) Prior Publication Data
US 2013/0242294 A1    Sep. 19, 2013

(30) Foreign Application Priority Data

Nov. 29, 2010   (JP) ................................ 2010-264802

(51) Int. Cl.
*G01N 21/956*   (2006.01)
*G01N 21/95*    (2006.01)
*G01N 21/84*    (2006.01)

(52) U.S. Cl.
CPC ........ *G01N 21/95623* (2013.01); *G01N 21/956* (2013.01); *G01N 21/9501* (2013.01); *G01N 2021/8477* (2013.01)

(58) Field of Classification Search
CPC ....................... G01N 21/956; G01N 21/95623
USPC ....................................................... 356/237.5
See application file for complete search history.

(56) References Cited

U.S. PATENT DOCUMENTS

| | | |
|---|---|---|
| 2006/0159330 A1 | 7/2006 | Sakai et al. |
| 2008/0015802 A1 | 1/2008 | Urano et al. |
| 2009/0290783 A1 | 11/2009 | Sakai et al. |
| 2010/0208249 A1 | 8/2010 | Shibata et al. |
| 2011/0310382 A1* | 12/2011 | Uto et al. .................. 356/237.2 |

FOREIGN PATENT DOCUMENTS

| | | | |
|---|---|---|---|
| JP | 2002-267615 | | 9/2002 |
| JP | 2006220644 | A * | 8/2006 |
| JP | 2007-33433 | | 2/2007 |
| JP | 2007-273513 | | 10/2007 |

(Continued)

*Primary Examiner* — Roy M Punnoose
(74) *Attorney, Agent, or Firm* — Baker Botts, LLP

(57) ABSTRACT

To prevent overlooking of a defect due to reduction in a defect signal, a defect inspection device is configured such that: light is irradiated onto an object to be inspected on which a pattern is formed; reflected, diffracted, and scattered light generated from the object by the irradiation of the light is collected, such that a first optical image resulting from the light passed through a first spatial filter having a first shading pattern is received by a first detector, whereby a first image is obtained; the reflected, diffracted, and scattered light generated from the object is collected, such that a second optical image resulting from the light passed through a second spatial filter having a second shading pattern is received by a second detector, whereby a second image is obtained; and the first and second images thus obtained are processed integrally to detect a defect candidate(s).

11 Claims, 11 Drawing Sheets

(56) References Cited

FOREIGN PATENT DOCUMENTS

| | | | |
|---|---|---|---|
| JP | 2008039533 A | * | 2/2008 |
| JP | 2008-268140 | | 11/2008 |
| JP | 2010-48730 | | 3/2010 |
| JP | 2010-175270 | | 8/2010 |

* cited by examiner

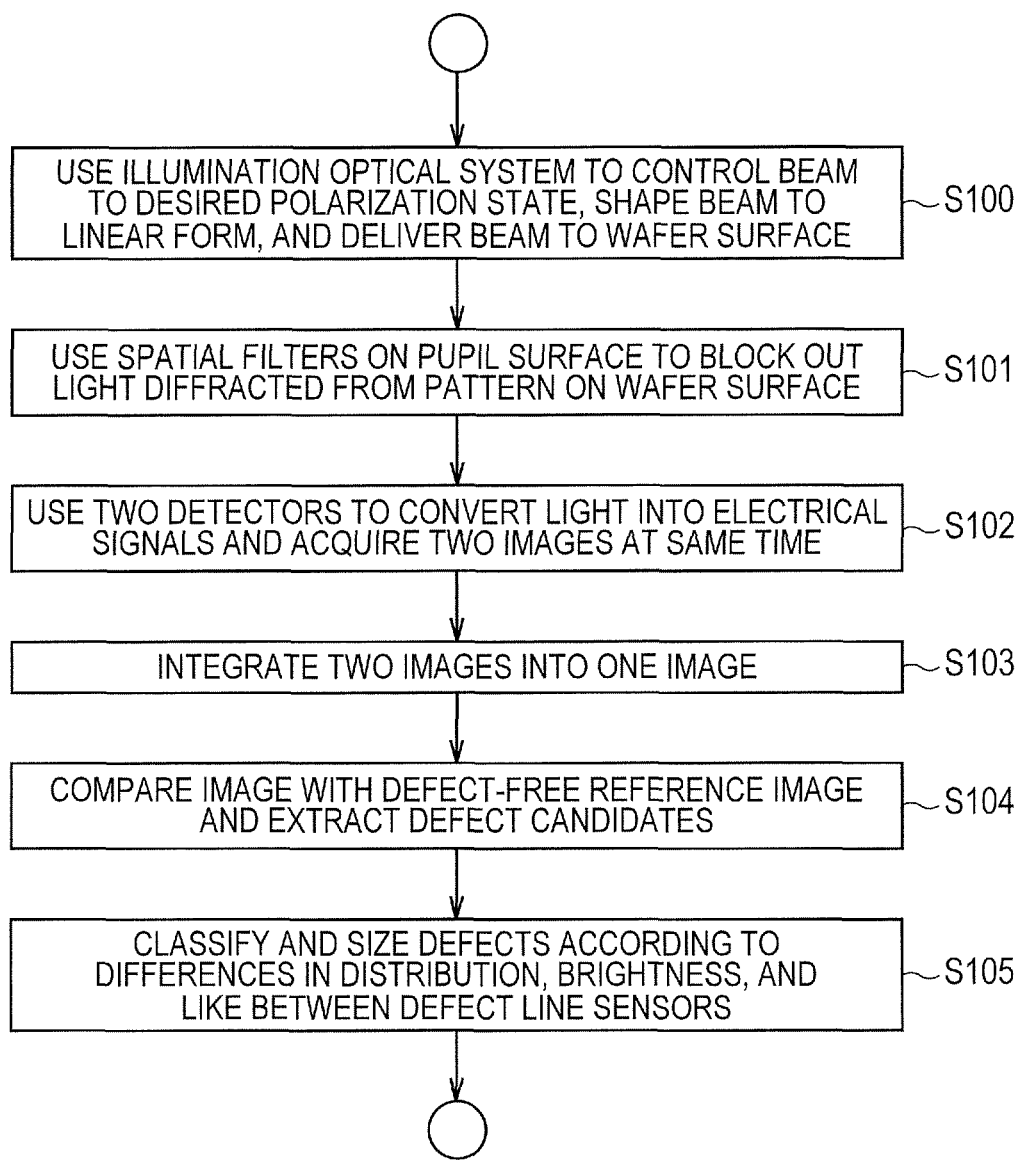

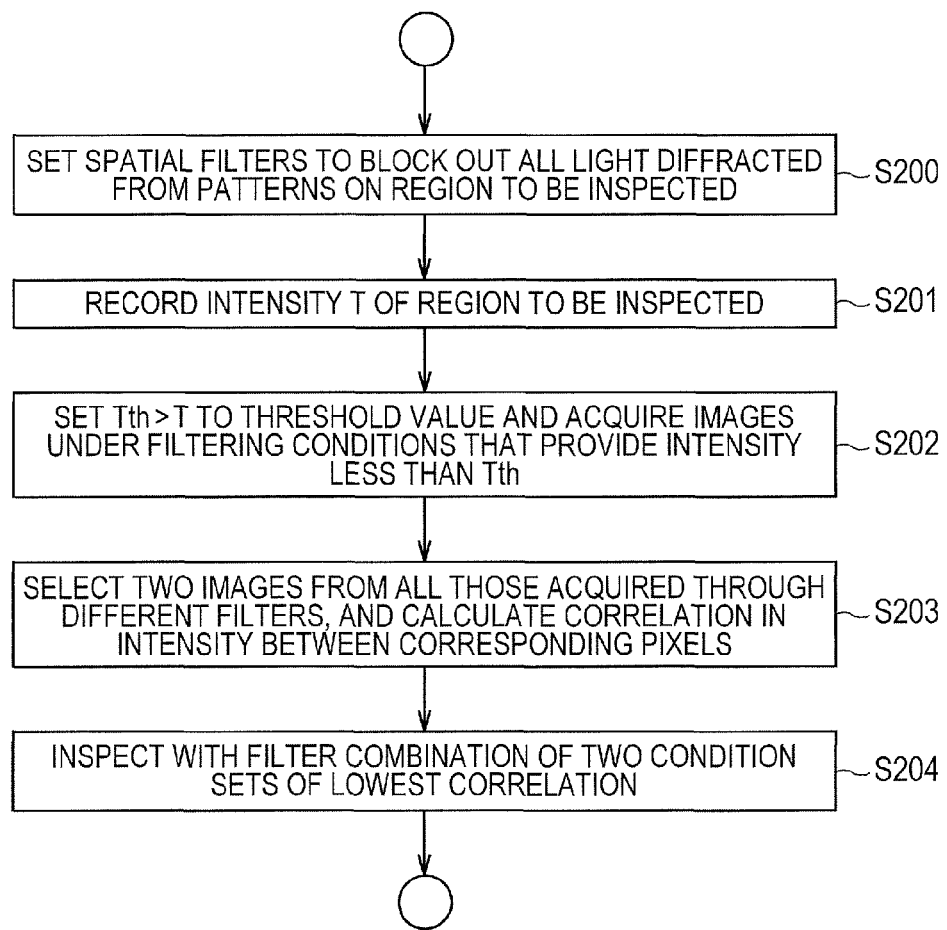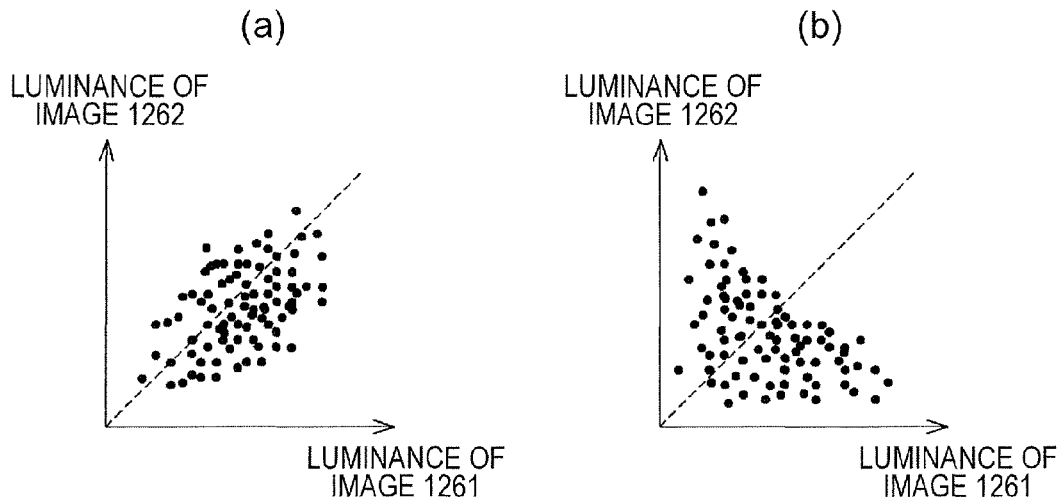

DEFECT INSPECTION DEVICE AND DEFECT INSPECTION METHOD

BACKGROUND

The present invention relates to a defect inspection device and defect inspection method for inspecting semiconductor wafers and liquid-crystal substrates.

When LSI or liquid-crystal substrates are manufactured, repetitive patterns are formed on objects to be worked (e.g., semiconductor wafers). During the manufacture of the LSI or liquid-crystal substrates, if foreign matter sticks to or defects occur on the surface of the work piece, this causes, for example, improper insulation of wiring, short circuiting, or other unwanted events. As finer-structured circuit patterns are formed in such manufacturing processes, non-defectives that are the patterns formed on work pieces are becoming difficult to discriminate from fine foreign matter or defects. The defects here are particles sticking to the sample that is the object to be inspected, crystal-originated particles (COPs), other crystal defects, scratches due to polishing, and other surface defects.

Patent Document 1 (JP-A-2007-273513) discloses a dark field defect inspection system and method in which, after a sample to be inspected has been irradiated with light admitted in an oblique direction, a diffraction pattern of the light diffracted from a repetitive circuit pattern present on the sample is blocked by a spatial filter previously set to assume a certain state. The inspection method includes the steps of, prior to defect inspection, using as a correction test object for re-setting the spatial filter the light diffracted from part of repetitive circuit patterns on the object to-be-inspected, measuring the amount of diffracted light that the spatial filter has reduced, comparing the amount of diffracted light with a threshold level, and re-setting the spatial filter so that the amount of diffracted light decreases to or below the threshold level.

Patent Document 2 (JP-A-2008-116405) discloses a dark field defect inspection system and method in which, after a sample to be inspected has been irradiated with light admitted in an oblique direction, a diffraction pattern of the light diffracted from a repetitive circuit pattern present on the sample is blocked by a spatial filter. The inspection method includes the step of observing the diffraction pattern, the step of recognizing the observed diffraction pattern by image processing, and the step of creating a spatial filter shape that is to block the recognized diffraction pattern.

SUMMARY

The inventions described in Patent Documents 1 and 2 are intended to improve defect detection sensitivity by blocking the light diffracted from a repetitive pattern. These inventions, however, have paid no attention to the fact that the insertion of the spatial filter for blocking the diffracted light is likely to cause the spatial filter to block out defect scattered light as well. This, in turn, has been likely to reduce a defect signal level and thus result in defects being overlooked.

An object of the present invention is to provide a defect inspection device and defect inspection method adapted to solve the foregoing problems associated with the cited prior art and prevent a decrease in defect signal level that might lead to a defect being overlooked.

Means for Solving the Problems

In order to attain the above object, the present invention is equipped with spatial filters of a minimum light-blocking area to block out light diffracted from an repetitive circuit pattern, and while maintaining the amount of light corresponding to a defect signal level, conducts image processing to remove noise components caused by diffracted-light leakage. The noise components caused by diffracted-light leakage depend on a shape and position of the spatial filter. Therefore, the invention integratedly processes two frames of image data obtained from different spatial filters which have blocked a part of the light diffracted from the repetitive circuit pattern, and thereby removes the noise components to improve defect detection sensitivity.

More specifically, in order to attain the above object, a defect inspection device according to an aspect of the present invention includes: illumination unit that irradiates an object to be inspected, with light, the object having patterns formed on a surface; light collecting unit that collects light reflected, diffracted, and scattered from the object irradiated with the light by the illumination unit; optical path branching unit that branches the light collected by the light collecting unit upon receiving the light reflected, diffracted, and scattered from the object into a first detection optical path and a second detection optical path; a first spatial filter fitted with a first light blocking pattern to block specific reflected, diffracted, and scattered light of the reflected, diffracted, and scattered light traveling towards the first detection optical path created as a result of branching by the optical path branching unit; first imaging unit that forms an image from the light passed through the first spatial filter; first image-acquisition unit that acquires a first image by detecting the image formed by the first imaging unit; a second spatial filter fitted with a second light-blocking pattern different from the first light blocking pattern, to block specific reflected, diffracted, and scattered light of the reflected, diffracted, and scattered light traveling towards the second detection optical path created as a result of branching by the optical path branching unit; second imaging unit that forms an image from the light passed through the second spatial filter; second image acquisition unit that acquires a second image by detecting the image formed by the second imaging unit; and image processing unit that conducts image processing to determine defect candidates by integratedly processing the first image acquired by the first image acquisition unit and the second image acquired by the second image acquisition unit.

More specifically, in order to attain the above object, a defect inspection method according to another aspect of the present invention includes: irradiating an object to be inspected, with light, the object having patterns formed on a surface; collecting light reflected, diffracted, and scattered from the object irradiated with the light; branching the collected light of the light reflected, diffracted, and scattered from the object into a first detection optical path and a second detection optical path; blocking, via a first spatial filter fitted with a first light blocking pattern, specific reflected, diffracted, and scattered light among the reflected, diffracted, and scattered light traveling towards the first detection optical path created as a result of branching; forming a first optical image from the light passed through the first spatial filter; acquiring a first image by detecting the formed first optical image with a first detector; blocking, via a second spatial filter fitted with a second light blocking pattern different from the first light blocking pattern, specific reflected, diffracted, and scattered light among the reflected, diffracted, and scattered light traveling towards the second detection optical path created as a result of branching; forming a second optical image from the light passed through the second spatial filter; acquiring a second image by detecting the formed second optical image with a second detector; and determining defect candidates by integratedly processing the acquired first image and second image.

In the present invention, the spatial filters of the minimum light blocking area block the light diffracted from repetitive circuit pattern, and while maintaining the amount of light corresponding to a defect signal level, conducts image processing to remove noise components caused by diffracted light leakage. The noise components caused by diffracted light leakage depend on a shape and position of the spatial filter. Therefore, the invention integratedly processes two frames of image data obtained from different spatial filters which have blocked a part of the light diffracted from the repetitive circuit pattern, and thereby removes the noise components to improve defect detection sensitivity.

These features and advantages of the invention will be apparent from the following more particular description of preferred embodiments of the invention, as illustrated in the accompanying drawings.

BRIEF DESCRIPTION OF THE DRAWINGS

FIG. 5 is a flow diagram showing a flow of processing in one of the first and second embodiments of the present invention;

FIG. 6 is a flow diagram that shows setting steps relating to the spatial filters in the first embodiment of the present invention;

Figure 8:
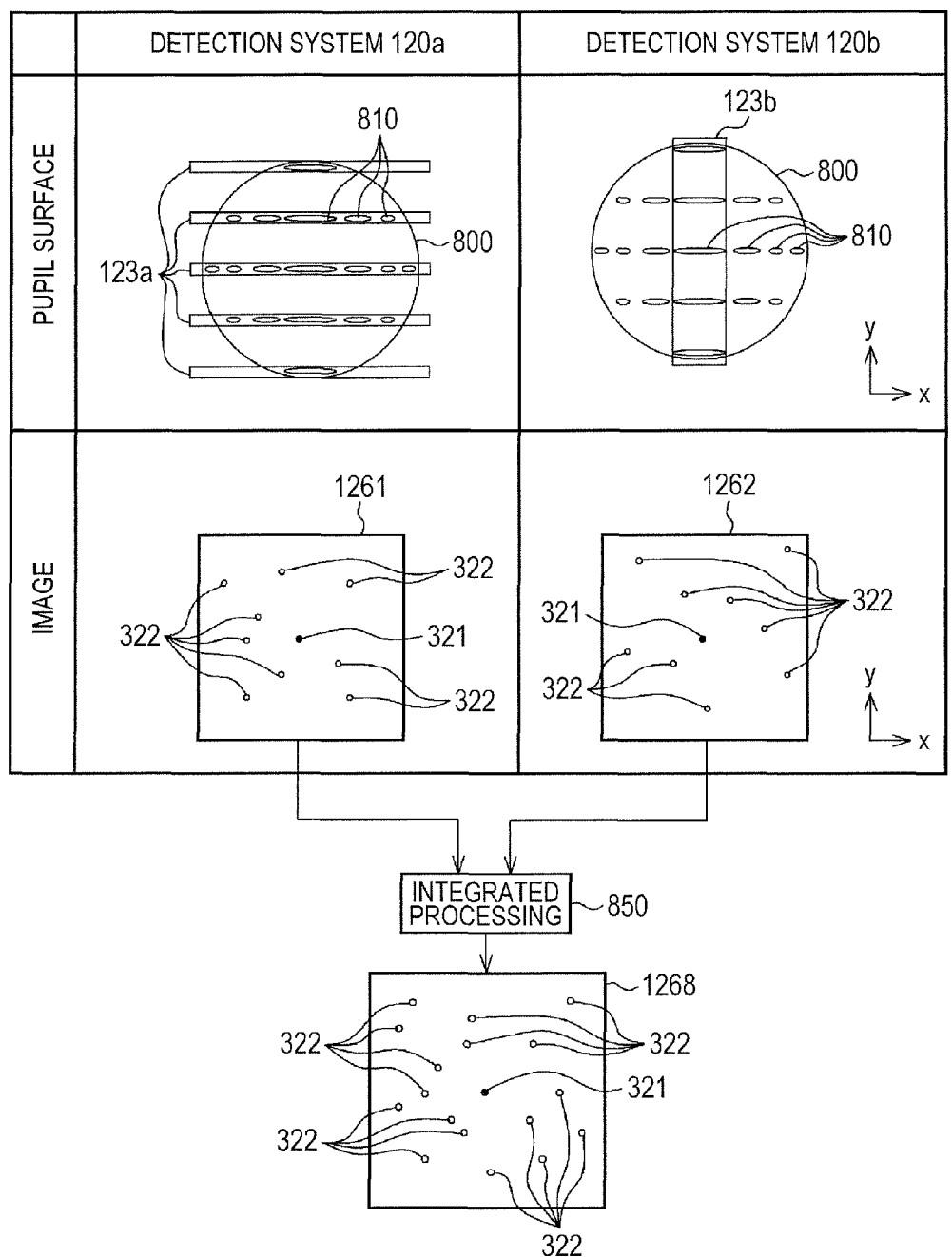
Figure 9:
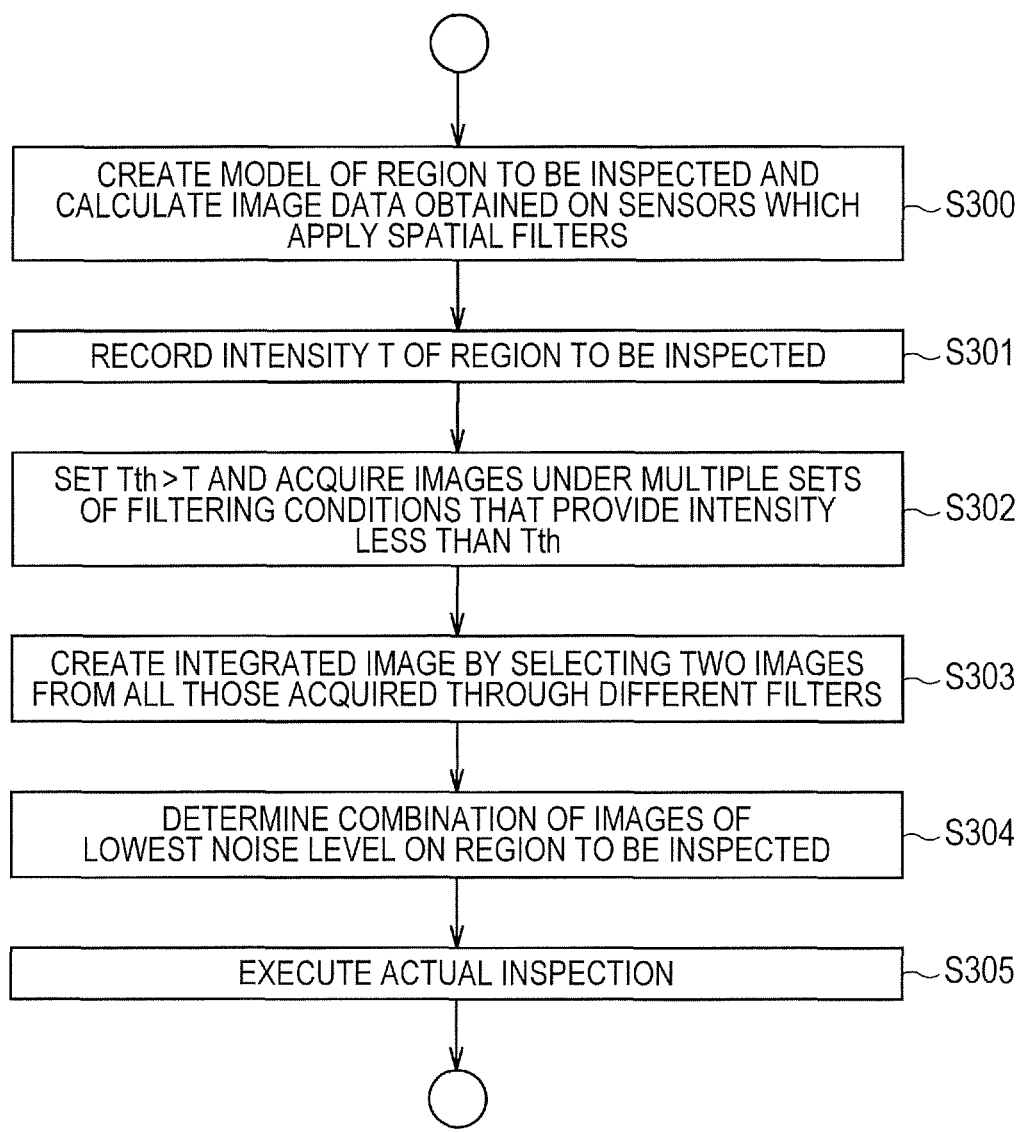
Figure 10:
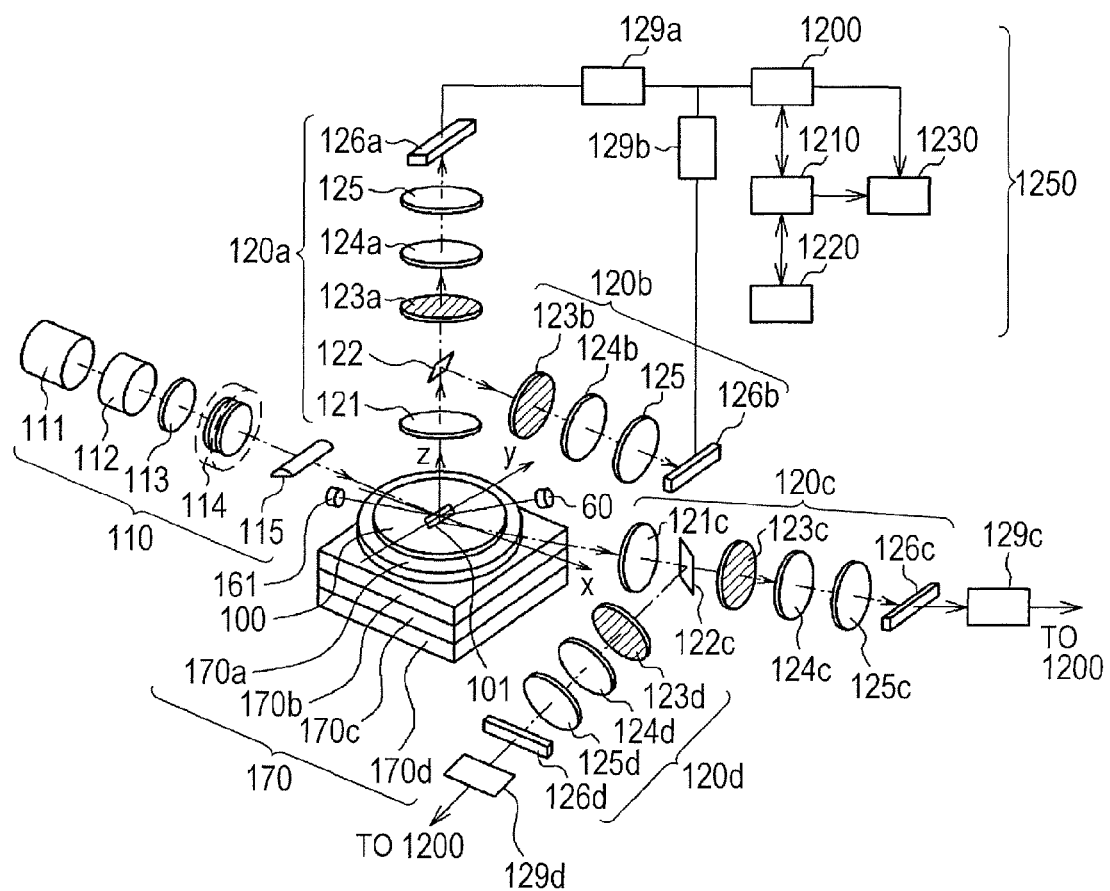
Figure 11:
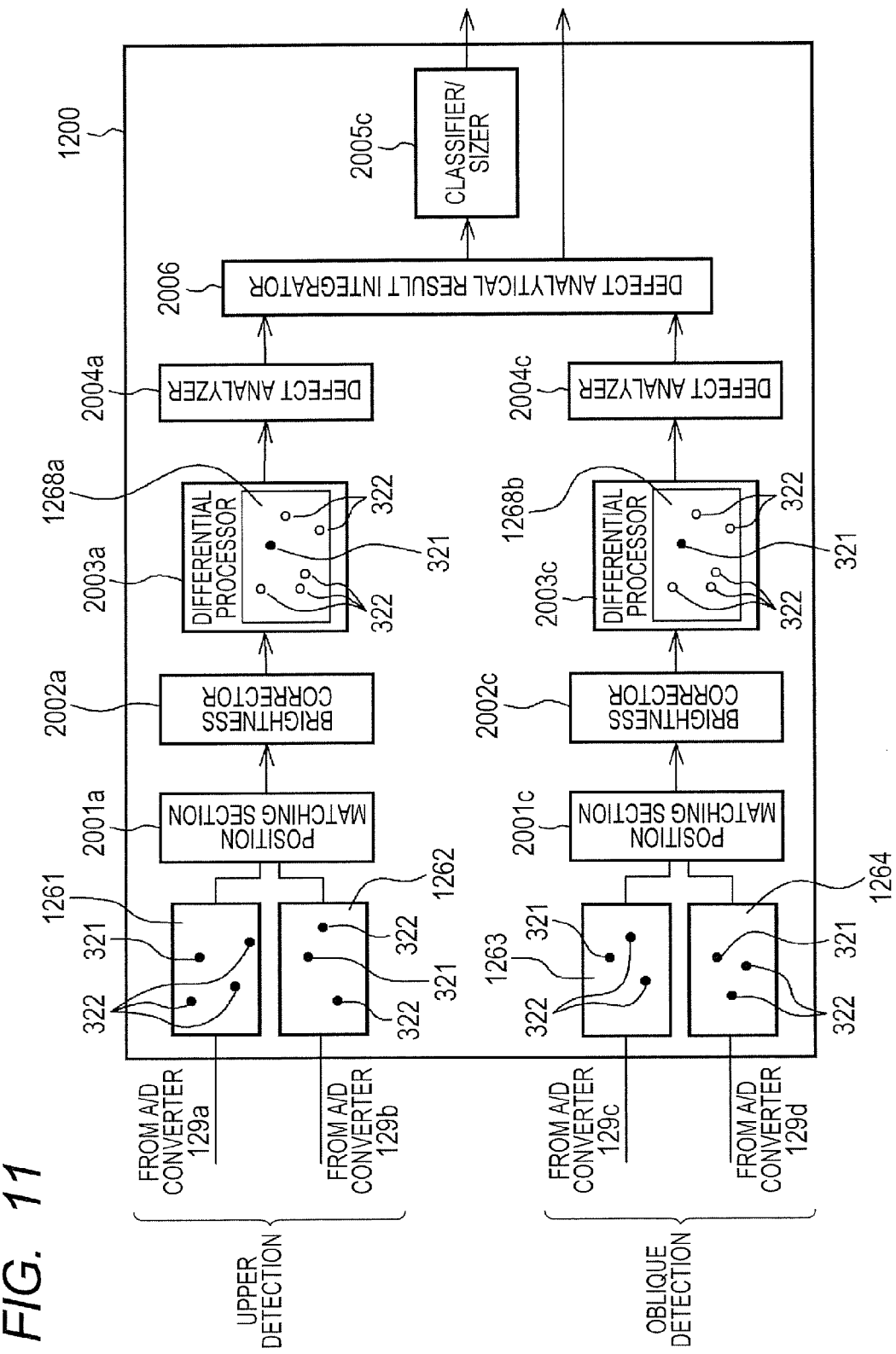
Figure 12:
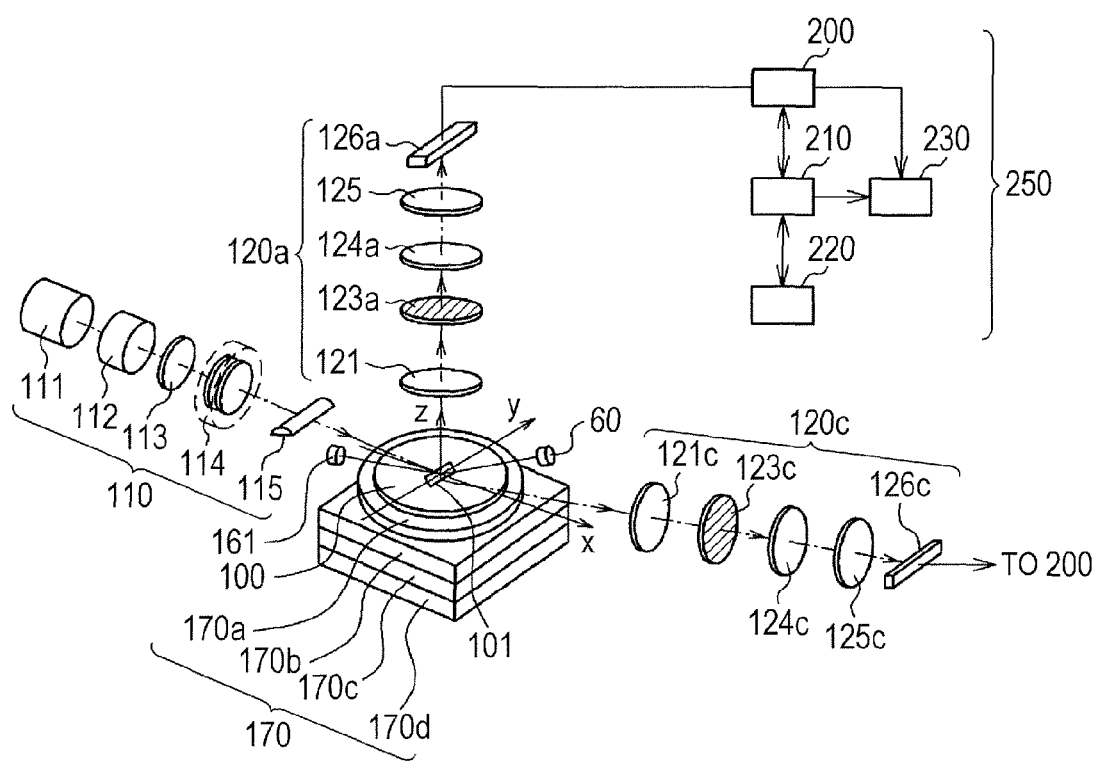

Section (a) of FIG. 7 is a graph showing a state in which any two images have a high degree of correlation in the first embodiment of the present invention, and section (b) of FIG. 7 is a graph showing a state in which any two other images have a low degree of correlation;

FIG. 8 is a diagram that represents relationships between spatial filter shapes and detection images in an optical inspection method according to the first embodiment of the present invention;

FIG. 9 is a flow diagram that shows setting steps relating to the spatial filters in the second embodiment of the present invention;

FIG. 10 is a block diagram schematically showing the optical inspection device configuration according to the third embodiment of the present invention;

FIG. 11 is a block diagram schematically showing an image processing unit configuration of the optical inspection device according to the third embodiment of the present invention; and FIG. 12 is a block diagram schematically showing the optical inspection device configuration according to the fourth embodiment of the present invention.

DESCRIPTION OF THE PREFERRED EMBODIMENTS

Embodiments of the present invention will be described hereunder using the accompanying drawings.

First Embodiment

A first embodiment of an optical inspection device according to the present invention is described below using FIGS. 1 to 6. Inspection of a semiconductor wafer by a dark-field inspection device is taken as an example in the following description.

Figure 1A:
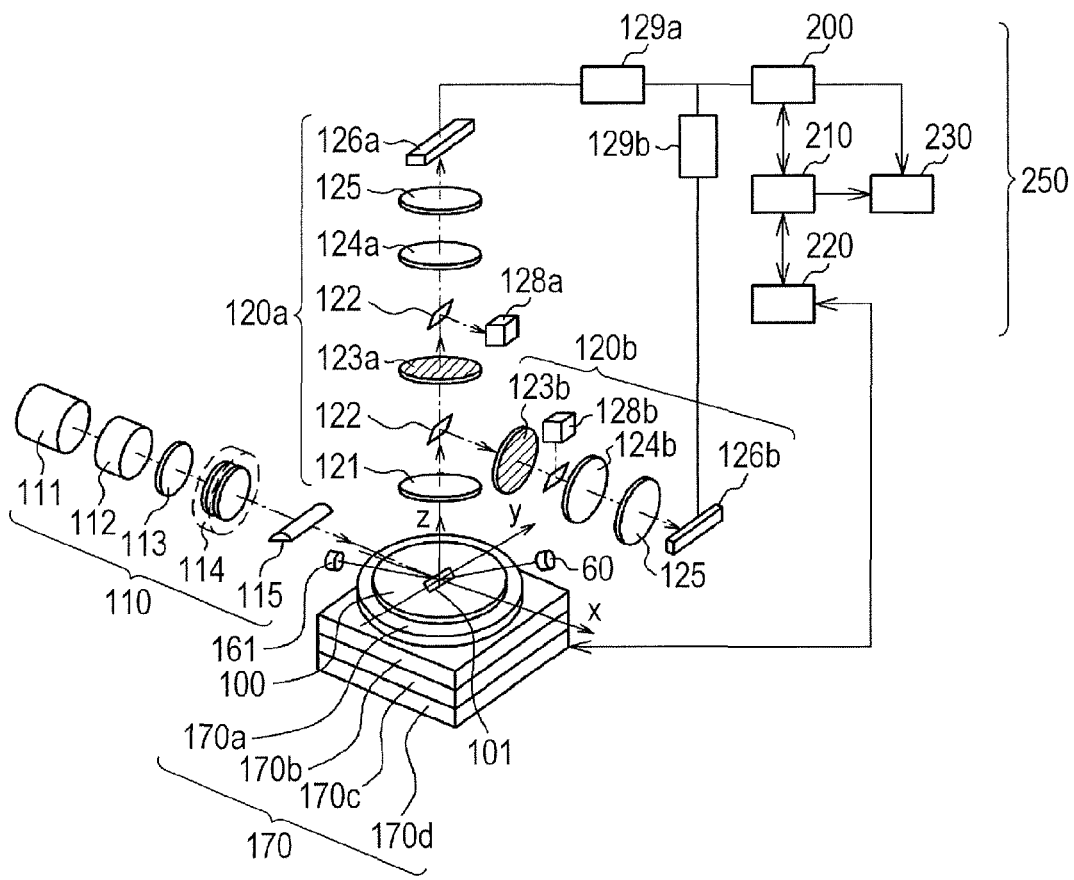
FIG. 1A is a block diagram that schematically shows optical inspection device configurations according to first and second embodiments of the present invention.

FIG. 1A is a block diagram showing the first embodiment of the optical inspection device according to the present invention. The optical inspection device according to the first embodiment includes an illumination optical system 110, a stage unit 170, imaging optical systems (detection optical systems) 120a and 120b, and a signal-processing and control system 250. The illumination optical system 110 irradiates an object to be inspected, or a sample (semiconductor wafer) 100, that is mounted on the stage unit 170, with illumination light in a direction inclined with respect to a direction normal to a surface of the semiconductor wafer 100 (this irradiation form is referred to as oblique illumination). The detection optical systems 120a and 120b detect the light scattered from the illuminated semiconductor wafer 100. Driving the stage unit 170 at that time in a plane causes the illumination light from the illumination optical system 110 to scan the surface of the semiconductor wafer 100 mounted on the stage unit 170. After the detection of the light scattered from the semiconductor wafer 100 by the optical systems 120a and 120b, the signal processing and control system 250 processes signal of the detected the scattered light and detects defects present on the semiconductor wafer 100.

(Illumination Optical System 110)

The illumination optical system 110 includes a laser light source 111, a neutral density (ND) filter 112, a beam expander 113, a polarization state generator 114 with a polarizer and a wave plate, and a linear beam generator 115 for irradiating the object to be inspected, or the semiconductor wafer 100, with a linear shaped beam of light.

The laser light source 111 emits a laser beam. The light source 111 at this time can be any one of a gas laser, a semiconductor laser, a solid-state laser, a surface-emitting laser, and the like. Useable wavelengths are of either an infrared range, a visible range, or an ultraviolet range. Since shorter wavelengths provide higher optical resolution, however, light of the ultraviolet range, such as UV (Ultra-Violet) radiation, DUV (Deep Ultra-Violet) radiation, VUV (Vacuum Ultra-Violet) radiation, or EUV (Extreme Ultra-Violet) radiation is preferably used to view microscopic defects.

The beam shaper 113 shapes the laser beam that has been emitted from the laser light source 111. In the present embodiment, the beam shaper 113 includes, as shown in FIGS. 1B and 1C, a beam expander 1131 that expands a diameter of the laser beam emitted from the laser light source 111, and a collimating lens 1132 that shapes the expanded laser beam into parallel light.

The polarization state generator 114, including the polarizer 1141 and the wave plate 1142, controls polarization characteristics of the light whose beam diameter has been expanded by the beam expander 1131 of the beam shaper 113. The linear beam generator 115 installs a cylindrical lens 1151.

Figure 1B:
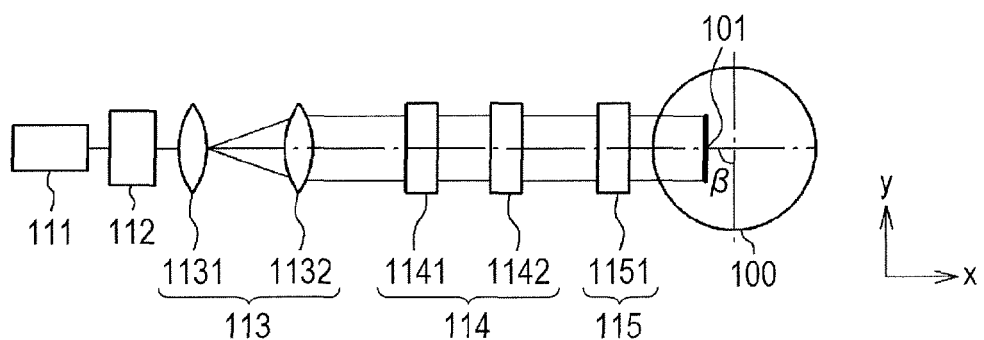
FIG. 1B is a plan view of an illumination optical system used in an optical inspection device configuration according to any one of the first to fourth embodiments of the present invention.
Figure 1C:
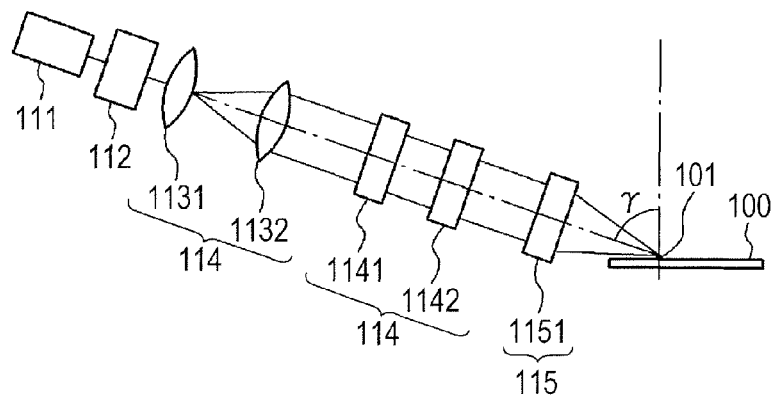
FIG. 1C is a side view of the illumination optical system used in the optical inspection device configuration according to any one of the first to fourth embodiments of the present invention.

FIG. 1B is a plan view of the illumination optical system 110, and FIG. 1C is a front view thereof.

In the above configuration, the laser beam emitted from the laser light source 111 is controlled in the amount of light by the ND filter 112, then expanded in beam diameter by the beam expander 1131 of the beam shaper 113, and shaped into parallel light by the collimating lens 1132 of the beam shaper 113. The polarization state of the parallel light is then controlled by the polarization controller 114 and is converged in one direction by the cylindrical lens 1151 of the linear beam generator 115. The converged light that has become a linear beam 101 parallel to a y-axis is then used to irradiate a linear region on the surface of the semiconductor wafer 100. An illumination angle β from the y-axis of the illumination optical system, shown in FIG. 1B, can be changed to an arbitrary direction including the y-axis direction. In addition, any value ranging between 0 and 90 degrees can be selected as a polar angle γ, which is an angle from a z-axis of the illumination optical system, shown in FIG. 1C.

At this time, the polarization state generator 114 may be placed at rear part of the linear beam generator 115. In this case, since the beam whose polarization state has been controlled by the polarization state generator 114 does not pass through a lens, this beam can be used to irradiate the semiconductor wafer 100 without a deviation of position due to aberration of a lens.

The surface of the semiconductor wafer 100 is irradiated with the thus-formed linear shaped beam 101 so that the y-direction of the stage is a lengthwise direction of the linear beam 101.

(Detection Optical Systems 120a and 120b)

The configuration shown in FIG. 1A includes two detection optical systems, 120a and 120b. Since the detection optical systems 120a and 120b have the same functionality, details of the detection optical system 120a are described here.

The detection optical system 120a includes an objective lens 121, a spatial filter 123a, a polarization state analyzer 124a, an imaging lens 125, and a line sensor 126a. A beam splitter 122 between the objective lens 121 and spatial filter 123a present in an optical path splits the optical path. A light passing through the beam splitter 122 forms an optical path leading to the detection optical system 120a, and a light reflected by the beam splitter 122 forms an optical path leading to the detection optical system 120b. The detection optical systems 120a and 120b have pupil-observing optics 128a and 128b, respectively, to observe exit pupils of the respective objective lenses 121. The inspection device guides light from the optical detection systems 120a and 120b to the pupil-observing systems 128a and 128b, respectively, via beam samplers 127a and 127b movable into and out from the optical paths of the optical detection systems 120a and 120b. If a relationship between positions and shapes of the spatial filters 123a and 123b, instead of those of the pupil observing systems 128a and 128b, and intensity of an image acquired by a line sensor, is predetermined and intensity distributions at positions of pupils can be recognized from that relationship, the pupil observing systems 128a and 128b for directly observing the pupil planes can be omitted.

The objective lens 121 collects the light reflected, scattered, and diffracted from the semiconductor wafer 100.

The spatial filter 123a blocks a part of the light reflected, scattered, and diffracted from the semiconductor wafer 100 and collected by the objective lens 121. The spatial filter 123a is placed at the exit pupil position of the objective lens 121 or at a position equivalent (conjugate) to the pupil position. The spatial filter 123a is, for example, a bar shaped light blocking filter that can be disposed in plurality (quantitatively and in terms of thickness) in vertical or horizontal directions, or a filter that enables light to two dimensionally pass through, and/or, to be two dimensionally blocked in, a desired region on the pupil plane. An element that utilizes electro optical effects, such as a liquid crystal, or a micro electro mechanical systems (MEMS) device, or the like is used as a two dimensional filter, in particular.

In the present embodiment, the linear beam generator 115 converges the illumination light in the y-direction to form a linear beam of light whose lengthwise direction is the y-direction. A diffraction pattern depending on a light-collecting numerical aperture (NA) and having a spread in the y-direction is therefore formed on the pupil plane. In this case, the bar-shaped filter disposed in one direction can appropriately eliminate the diffracted light.

The polarization state analyzer 124a controls the polarization characteristics of the scattered light which has not been blocked by the spatial filter 123a. The polarization state generator 124a includes, for example, a quarter-wave plate, a half-wave plate, and a polarizer, each of which is rotationally controlled in separate form and enables any polarized light to pass through.

The imaging lens 125 transmits the scattered light that has not been blocked by the spatial filter 123a, and forms an optical image of the light. Positions of the spatial filter 123a and imaging lens 125 here may be reversed.

The line sensor 126a is placed in such a position that the image of the scattered light that has been formed by the imaging lens 125 is once again formed on a detection surface of a line sensor 126a, and the sensor 126a detects an optical image of the scattered light. The line sensor 126a can be any one of, for example, a TDI (Time-Delayed Integration) image sensor, a CCD (Charge-Coupled Device) sensor, a CMOS (Complementary Metal-Oxide Semiconductor) sensor, and the like.

An analog output signal from the line sensor 126a, which is based on the scattered light that has thus been detected, is amplified into digital signal form by an A/D converter 129a and then transmitted to the signal-processing and control system 250, for processing.

Substantially the same also applies to the detection optical system 120b. That is to say, the optical image of the scattered light from the semiconductor wafer 100 is detected and then transmitted to the signal processing and control system 250, for processing. The region where the spatial filter 123b is to block the light is set to differ from that of the detection optical system 120a in terms of shape and position, and two images under different optical conditions are acquired at the same time. In this case, since noise components contained in the image which the line sensor 126a or 126b detects differ from each other according to particular shapes and positions of the spatial filters 124a and 124b, integrated processing of the two images allows acquisition of an image with suppressed noise and hence, improvement of defect detection performance. A method of setting the spatial filters 123a and 123h will be described later herein.

(Stage Unit 170)

The stage unit 170 includes an x-stage 170a, a y-stage 170b, a z-stage 170c, and a θ-stage 170d.

The x-stage 170a moves in an x-direction with the semiconductor wafer 100 mounted thereon. The semiconductor wafer 100 is the object to be inspected that has fine patterns formed on the surface.

Likewise, the y-stage 170b, the z-stage 170c, and the θ-stage 170d move in a y-direction, a z-direction, and a θ-direction, respectively, with the semiconductor wafer 100 mounted thereon. The semiconductor wafer 100 is the object to be inspected that has the fine patterns formed on the surface.

(Signal-Processing and Control System 250)

The signal processing and control system 250 includes an image processing unit 200, an operating unit 210, a control unit 220, a display unit 230, and a height detection unit 160.

The image processing unit 200 produces images 1261 and 1262 of scattered light from a digital signal formed by amplification in A/D converters 129a and 129b following completion of detection in the line sensors 126a and 126b. The image processing unit 200 also processes the produced images 1261 and 1262 of the scattered light from the semiconductor wafer 100 and extracts surface defects.

Figure 2:
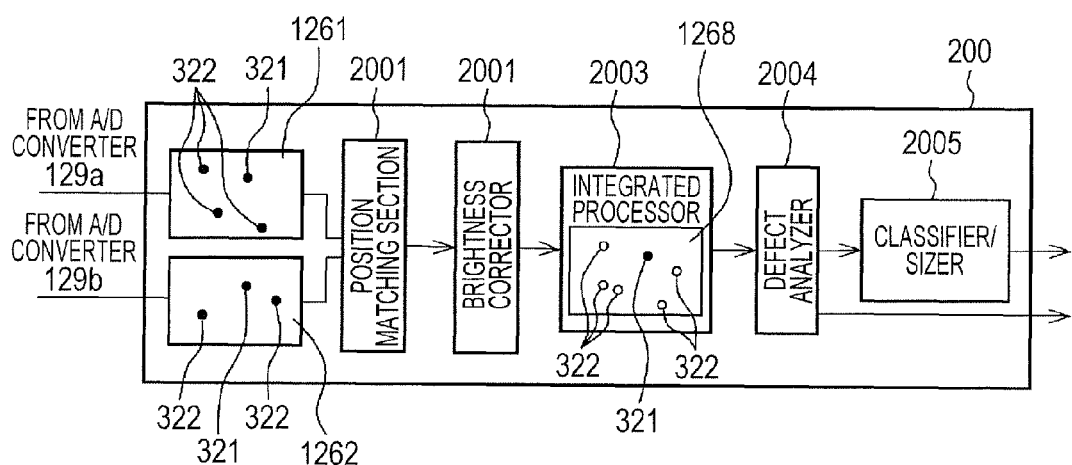
FIG. 2 is a block diagram schematically showing an image-processing unit configuration of the optical inspection device according to one of the first and second embodiments of the present invention.

FIG. 2 is a block diagram schematically showing a configuration of the image processing unit 200 in the first embodiment of the optical inspection device according to the present invention. First, the image processing unit 200 uses position information on the y-stage 170b to generate an image 1261 based on the scattered light acquired in the detection optical system 120a, and an image 1262 based on the scattered light acquired in the detection optical system 120b. A position-matching element 2001 matches positions of the generated images 1261 and 1262 with accuracy less than pixel units. A brightness corrector 2002 corrects the position matched images 1261 and 1262 for a difference in brightness therebetween due to differences in efficiency between the light passed through the beam splitter 122 and the light reflected therefrom, in transmittance between the polarization state analyzers 124a and 124b, in transmittance between the detection lenses 125, and in efficiency between the line sensors 126a and 126b. An integration processor 2003 constructs one image 1268 by integrating the two images, 1261 and 1262, which have been corrected for the difference in brightness. For example, when the integration processor 2003 integrates the images 1261 and 1262 corrected for the difference in brightness, the integration processor 2003 provides weighted addition, multiplication, or the like, to construct the image 1268. The images 1261 and 1262 were obtained by assigning different conditions (different filtering patterns) to the spatial filters 123a and 123b for blocking the light scattered from the semiconductor wafer 100. Although defect signals 321 in the images acquired under the different conditions share commonality in that both shine, since the way any noise components 322 contained in the images shine varies from region to region, the noise components 322 in the image 1268 that has been obtained by integration are reduced and the defect signals 321 become apparent.

Next, a defect analyzer 2004 extracts defects from the newly constructed image 1268. The defect analyzer 2004 extracts defect candidates by comparing the image 1268 with a reference image (not shown) that is obtained by integrating, similarly to the images 1261 and 1262, the images that the line sensors 126a and 126b obtained by imaging either the adjacent patterns originally formed into the same shape, or the patterns at the same position on adjacent dies. Arithmetic subtraction between the image 1268 and the reference image is performed during the comparison. At this time, since the light scattered from defects differs from the light scattered from non-defective regions, an image with enhanced intensity of the defect scattered light is obtained. In other words, an image in which the non-defective regions are dark and the defective regions are bright is obtained, so that the derived differential image can be provided with threshold processing for defect analysis. The image to be subjected to threshold processing is determined from, for example, statistical brightness of a plurality of non-defective regions. Next, a defect classifier/sizer 2005 analyzes, classifies, and sizes each defect from scattered-light distribution states, intensity levels, and other factors of the extracted defect candidates.

Figure 3:
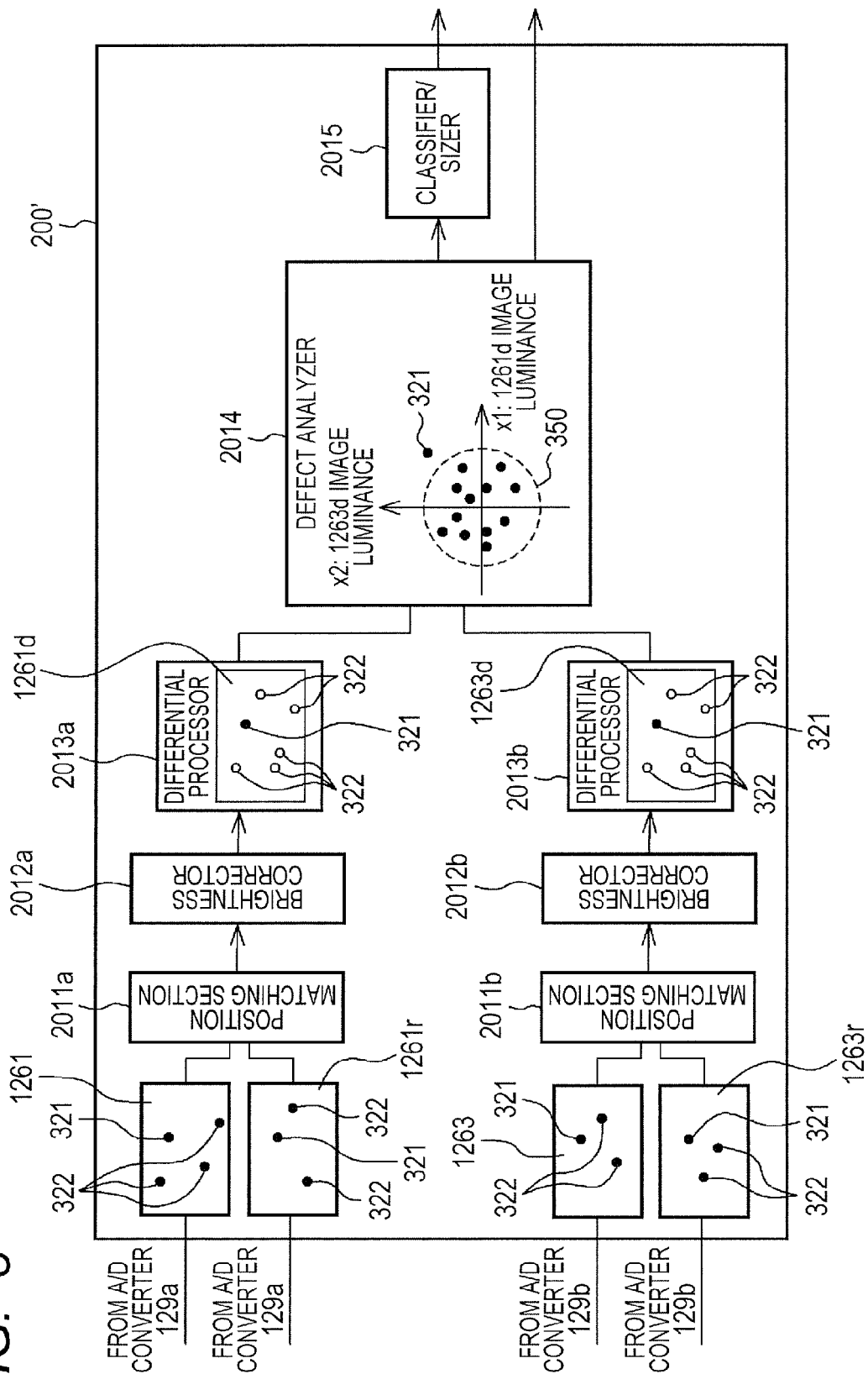
FIG. 3 is a block diagram showing a first modification of the image processing unit used in the optical inspection device according to one of the first and second embodiments of the present invention.

A first modification of the image processing unit 200 is shown in FIG. 3. The image processing unit 200' in the first modification first generates an image 1261 based on the scattered light acquired in the detection optical system 120a, and a reference image 1261r acquired in a region of the same shape as that of the location where the image 1261 was acquired on the adjacent dies, cells, or the like. Next, a position matching element 2011a matches positions of the generated images 1261 and 1261r with accuracy less than sensor pixel units. After position matching, a brightness corrector 2012a corrects the position matched inspection image 1261 and reference image 1261r for a difference in brightness therebetween due to the sample's characteristics such as a difference in thickness of a thin film between the sample surface and the surface layer, or due to optical reasons such as a difference in height between the inspection lenses and the wafer. After this, an integrated processor 2013a conducts differential processing based on arithmetic subtraction between corresponding pixels in the inspection image 1261 and the reference image 1261r, thereby to obtain a differential image 1261d. In this case, the reference image 1261r that has been generated using the scattered light acquired by the detection optical system 120a on the region of the same shape as that of the location where the image 1261 was acquired on the adjacent dies, cells, or the like, is temporarily stored into an image memory not shown. Then, the reference image 1261r is called up from the image memory into the position matching element 2011a, and position matching is carried out between the reference image 1261r and the inspection image 1261, with accuracy less than pixel units. In addition, an image 1263 that includes defects, and a reference image 1263r are created from the signal that the detection optical system 120b acquired. The image 1263 and the reference image 1263r also undergo processing in substantially the same processing unit configuration, whereby a differential image 1263d is then obtained.

Next, a defect analyzer 2014 constructs an orthogonal coordinate system with luminance of the differential image 1261d taken on a horizontal axis x1 and luminance of the differential image 1263d on a vertical axis x2, and plots corresponding pixel luminance levels of the differential images 1261d and 1263d in the orthogonal coordinate system. In the x1, x2 space of the orthogonal coordinate system, since noise is a remainder of the subtraction between the defect image and the reference image, both x1 and x2 components are low in noise level and distributing near an origin. The luminance of the defect image, on the other hand, is high relative to the noise level and plotted at positions distant from the origin in the x1, x2 space. Accordingly, the noise components 322 and the defect 321 are separated by providing a boundary 350 near the origin of the orthogonal coordinate system, to analyze the defect. The boundary 350 can be a combination of circles, lines, or the like. To use a circle, for example, a radius can be expressed as A and a boundary line can be drawn in a region that satisfies numerical expression 1.

(Numerical expression 1)

$$\sum_i x_i^2 = A^2 (i = 1, 2)$$ Expression 1

While an example of processing two images has been shown and described in the present embodiment, similar processing can be achieved by using three images or more. The classifier/sizer 2015 analyzes, classifies, and sizes each of the extracted defect candidates on the basis of the respective scattered light distribution states, intensity, and other features and characteristics.

Figure 4:
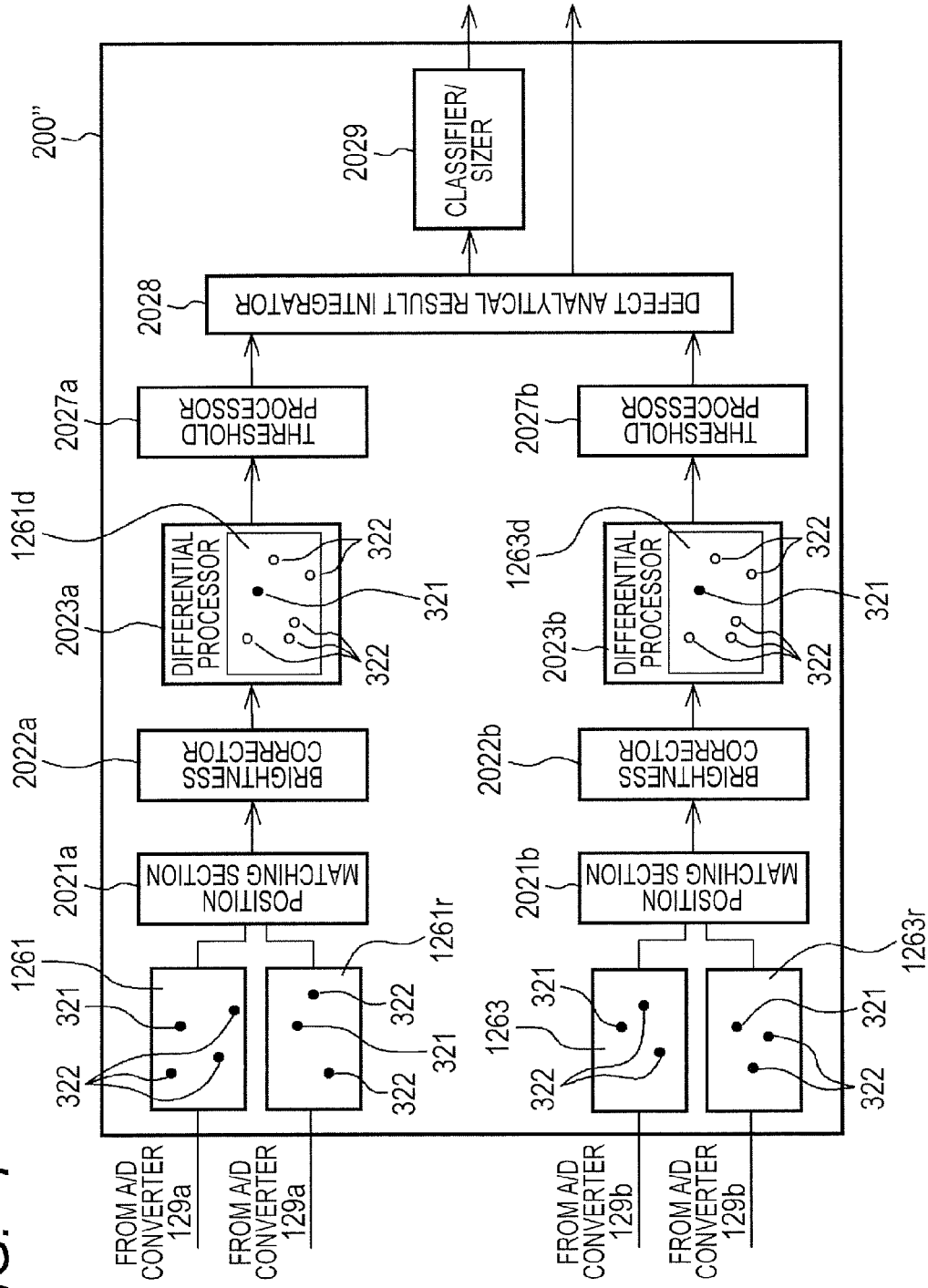
FIG. 4 is a block diagram showing a second modification of the image processing unit used in the optical inspection device according to one of the first and second embodiments of the present invention.

A second modification of the image processing unit 200 is shown in FIG. 4. The image processing unit 200" in the second modification first generates an image 1261 based on the scattered light acquired in the detection optical system 120a, and a reference image 1261r acquired in the region of the same shape as that of the location where the image 1261 was acquired on the adjacent dies, cells, or the like. Next, a position matching element 2021a matches positions of the generated images 1261 and 1261r with accuracy less than sensor pixel units. After position matching, a brightness corrector 2022a corrects the position matched inspection image 1261 and reference image 1261r for the difference in brightness therebetween due to the sample's characteristics such as the difference in a state of the sample surface and/or thickness of the thin film surface layer, or due to optical reasons such as the difference in height between the inspection lenses and the wafer. After this, an integrated processor 2023a conducts differential processing based on the arithmetic subtraction between the corresponding pixels in the inspection image 1261 and the reference image 1261r, thereby to obtain the differential image 1261d. Processing up to obtaining the differential image 1261d is the same as in the first modification described in FIG. 3.

Next, a threshold processor 2027a provides the differential image 1261d with a threshold processing to set up a threshold level and extract all luminescent spots exceeding the threshold level, as defect candidates. The threshold level is determined from, for example, the statistical brightness of a plurality of non-defective regions. The defect inclusive image 1263 generated from the scattered light acquired in the detection optical system 120b, and the reference image 1263r are processed in processors 2021b to 2023b in substantially the same manner as done in the processors 2021a to 2023a, and a differential image 1263d is obtained. After this, a threshold processor 2027b extracts defect candidates. Next, a defect analytical result integrator 2028 integrates the defect candidates that the threshold processors 2027a and 2027b have extracted from the differential images 1261d and 1263d, respectively. For example, the integration uses common sections of the defect candidates extracted from the differential images 1261d and 1263d. Finally, a classifier/sizer 2029 analyzes, classifies, and sizes each of the extracted defect candidates on the basis of respective scattered light distribution states, intensity, and other features and characteristics.

The operating unit 210, a section that an operator operates the inspection device, is used for purposes such as creating inspection recipes, directing inspection instructions based on the created recipes, displaying a map of inspection results, and displaying feature quantities of detected defects.

The control unit 220 controls each section of the device. For example, the control unit 220 receives detection results from the height detection unit 160 described later, controls positions of the x-stage 170a, y-stage 170b, z-stage 170c, and θ-stage 170d of the stage unit 170, and sends control signals to the spatial filters 123a and 123b and the polarization state analyzers 124a and 124b.

The height detection unit 160 detects the directly reflected beam of light delivered from a laser light transmitter 161 such as the semiconductor laser, to the surface of the semiconductor wafer 100 to be inspected, obtains position information about this reflected light on the detection surface, detects stage height of the stage unit 170 during the inspection from the position information obtained, and sends detection results to the control unit 220. If the stage height is inappropriate, the z-stage 170c is driven according to the particular detection results of the height detection unit by using a control signal from the control unit 220 to correct the inappropriateness of the stage height and hence to prevent defocusing of the wafer.

FIG. 5 is a flow diagram showing a first example of an optical inspection method according to the present invention. In the illumination optical system 110, the ND filter 112 controls the amount of light of a laser beam emitted from the laser light source 111, next the beam shaper 113 expands the beam diameter and forms a beam parallel to the optical axis, and the polarization state generator 114 obtains a desired polarization state. After this, the linear beam generator 115 shapes the light into linear form and then the semiconductor wafer 100 continuously moving by the x-stage 170a in the x-direction is irradiated with the linearly formed illumination light in an oblique direction. The sequence from controlling the amount of light to irradiating the wafer with the linear illumination light forms the step S100. After the irradiation, the linearly formed illumination light is reflected, scattered, and diffracted from the semiconductor wafer 100. The spatial filter 123a or 123b placed near the exit pupil position of the objective lens 121 blocks, of the light thus incident upon the objective lens 121, only the light that has been reflected, scattered, and diffracted from repetitive patterns formed on the semiconductor wafer 100. The blocking of the light is step S101. The detection optical systems 120a and 120b acquire two optical images at the same time by detecting these images created from the light that has not been blocked by the spatial filter 123a or 123b after being reflected, scattered, and diffracted from the semiconductor wafer 100. The simultaneous acquisition of the two images is step S102. The image-processing unit 200 generates one image by integrating the two images (step S103), then compares the integrated image with a previously created reference image and extracts defect candidates (step S104), and classifies and sizes each of the extracted defect candidates according to particular differences in a distribution state of each defect candidate between the detected images, differences in brightness, and other information (step S105).

Next, detailed operation in each step is described below.
(Step S100)

In step S100, the beam shaper 113 shapes the laser beam emitted from the light source 111 of the illumination optical system 110, and then the polarization state generator 114 controls the polarization state. After this, the linear shaped beam generator 115 forms the light into a linear shaped beam and irradiates the semiconductor wafer 100 with the linear shaped beam. At this time, the optical dark-field inspection device activates the control unit 220 to control the y-stage 170b for a movement at a constant speed in the y-direction or a minus (−) y-direction, thereby while continuously moving the semiconductor wafer 100 in that direction with respect to the illumination optical system 110 and the detection optical systems (120a and 120b), irradiates the surface of the semiconductor wafer 100 with the illumination light and scans the light across the wafer surface.

(Step S101)

In step S101, part of the light reflected, scattered, and diffracted from the region on the semiconductor wafer 100 that has been irradiated with the linear shaped beam enters and is condensed by the objective lens 121 of the detection optical systems 120a and 120b, and the optical path is branched by the beam splitter 122. Of the light that has thus been condensed, light that has passed through the beam splitter 122 travels along the optical path of the detection optical system 120a and reaches the spatial filter 123a. Optical patterns generated by the light reflected, scattered, and diffracted from the repetitive patterns formed on the surface of the semiconductor wafer 100 are blocked out by a light blocking pattern formed on the spatial filter 123a. Light that has not been blocked by the spatial filter 123a and has passed therethrough is incident in the polarizing controller 124a, in which the polarization state of the light is controlled, and the polarization state controlled light exits the polarizing controller 124a. After this, the imaging lens 125 forms an image of the scattered light that has not been blocked by the spatial filter 123a. The image of the scattered light is detected by the line sensor 126a which is placed so that the detection surface of the line sensor 126a is positioned at the place where the image of the scattered light is formed. Of the light that has been branched by the beam splitter 122, on the other hand, light that has been reflected therefrom travels along the optical path of the detection optical system 120b and reaches the spatial filter 123b. Optical patterns generated by the light reflected, scattered, and diffracted from the repetitive patterns formed on the surface of the semiconductor wafer 100 are blocked out by a light blocking pattern formed on the spatial filter 123b. Light that has not been blocked by the spatial filter 123b and has passed therethrough is incident in the polarizing controller 124b, in which the polarization state of the light is controlled, and the polarization state controlled light exits the polarizing controller 124b. After this, the imaging lens 125 forms an image of the scattered light that has not been blocked by the spatial filter 123b. The image of the scattered light is detected by the line sensor 126b placed so that the detection surface is positioned at the place where the image of the scattered light is formed. The method of setting the spatial filters will be described later herein.

(Step S102)

In step S102, the signals that the line sensors 126a and 126b generated by detecting the images of the scattered light whose polarization characteristics were controlled in step S101 undergo A/D conversion by the A/D converters 129a and 129b, and after this, enter the image processing unit 200, in which two images relating to the surface of the semiconductor wafer 100 are then created.

(Step S103)

In step S103, the position matching element 2001 matches positions of the two images that were created in step S102, with accuracy less than the pixel units of the line sensors 126a and 126b, then the brightness corrector 2002 corrects the position matched images for a difference in brightness, and the integration processor 2003 generates a new image by integrating the two images that have been corrected in brightness (for further details of the image generation, see the above description of the image-processing unit 200).

(Step S104)

In step S104, the defect analyzer 2004 compares the image that was generated by the integration in step S103, with a reference image that has been stored into a storage unit not shown (for further details of this comparison, see the above description of the image processing unit 200), and extracts defect candidates on the basis of the difference that is a result of the comparison.

(Step S105)

In accordance with a difference between distribution states on the line sensors 126a and 126b, a difference in brightness, and other information, the defect classifier/sizer 2005 classifies and sizes each of the defect candidates that were extracted in step S104.

In general, diffracted light occurs perpendicularly to the pattern structure. The semiconductor wafer 100, the object to be inspected, has a structure that mainly includes the patterns extending linearly in the directions of the x- and y-axes, the principal axes, of FIGS. 1A and 1B. The diffracted light occurs perpendicularly to the array direction of the linear patterns, and much of the diffracted light therefore exists in the x- and y-directions. Setting an appropriate elevation angle of the illumination in the illumination optical system 110 and an appropriate NA of the objective lens 121 in the detection optical system 120a or 120b allows the device to be configured so that entry of the amount of diffracted light from the linear patterns on the semiconductor wafer 100 into the detection optical system 120a or 120b will be minimized. The diffracted light entering the objective lens 121 can be filtered out with the spatial filters 123a and 123b.

In the present invention, differences between noise characteristics of images due to differences between parameter settings of the spatial filters 123a and 123b are utilized to suppress noise and actualize a defect signal. FIG. 6 is a flow diagram that shows setting steps relating to the spatial filters. In step S200, the spatial filters block out all of the light diffracted from the wafer region to be inspected. In step S201, average intensity T at the region to be inspected under the assigned conditions of the spatial filters is identified from the images acquired by the line sensors. In step S202, any value greater than the average intensity T is set as a threshold level "Tth". And a plurality of images are acquired under the spatial filtering conditions that give intensity less than "Tth" to the region to be inspected. In step S203, two of the acquired number (n) of images are selected and a correlation in the intensity at the inspection region between the two images is calculated for an nC2 number of combinations. In step S204, the spatial filtering conditions that allow acquisition of a combination of any two images having the lowest correlation are assigned to the spatial filters 123a and 123b and then the inspection is conducted.

Next, details of each step are described below.

(Step S200)

In step S200, the spatial filters are set so that the light diffracted from the patterns on the object to be inspected will all be blocked on the exit pupil plane of the objective lens. Setting is done in substantially the same way as that of spatial filter setting in any one of the conventional techniques described in Patent Documents 1 and 2. In the conventional inspection methods, inspection is executed under the spatial filtering conditions that block all of the diffracted light, and under these conditions, not only the pattern-diffracted light but also defect signals are blocked.

(Step S201)

In step S201, the line sensors acquire images using the spatial filters that were set in step S200, and average intensity T at the inspection target region with the diffracted light filtered out by the spatial filters is calculated. The line sensors used at this time may be replaced by, for example, observation cameras capable of calculating the average intensity at the inspection target region.

(Step S202)

In step S202, the average intensity T at the inspection target region that was calculated in step S201 is multiplied by a coefficient α, the "Tth" value expressed in terms of "Tth=Txa" is set as a threshold level, and the intensity at the region to be inspected is measured using the set "n" number of combinations of spatial filtering conditions that yield intensity values less than the threshold level. The coefficient α is set to obtain a defect detection signal permitting a certain degree of diffracted light leakage. At this time, if too great an α value is assigned, the defect signal will be buried in noise components, so α is set to be, for example, nearly 1.1 to detect microscopic defects equivalent to the average intensity T.

(Step S203)

In step S203, two combinations are selected from the "n" number of combinations of spatial filtering conditions that were determined in step S202, and a correlation calculation is conducted for each of the "nC2" number of combinations. Corresponding pixels in the two images selected as in sections (a) and (b) of FIG. 7 have respective brightness levels plotted in a biaxial space on a graph, and a correlation coefficient is calculated. A high correlation between the two images, as shown in section (a) of FIG. 7, indicates that each pixel resembles in a luminance level of noise and thus that even if the two images are integrated, this will only result in a similar image being created and will not be too effective for improving a signal to noise ratio (SNR). A low correlation, as shown in section (b) of FIG. 7, however, indicates that since each pixel differs in the luminance level of noise, the integration of the two images allows suppression of noise in luminance level and is thus expected to improve SNR (i.e., to actualize defects). Examples of images obtained when different spatial filters are applied are shown in FIG. 8. A plurality of luminescent spots 810 due to the patterns on the wafer are present on pupil plane 800. In the detection system 120a, the spatial filter 120a is set to block all luminescent spots 810. The image 1261 obtained at this time will decrease in the luminance of noise, and at the same time, part of the defect signal will also decrease in luminance because of blocking by the spatial filter 123a. In the detection system 120b, on the other hand, since only part of the luminescent spots 810 on the pupil plane 800 are blocked by the spatial filter 123b, the luminance of noise in the image 1262 obtained here will increase in comparison with the noise luminance in the image 1261, and at the same time, the luminance of the defect signal will also increase. Here, since the blocking positions of the luminescent spots 810 likely to be a noise-inducing factor on the pupil plane 800 differ between the images 1261 and 1262, a correlation of noise in the images 1261 and 1262 had a strong tendency to decrease. The integration processor 2003 conducts an integration process 850 upon the images 1261 and 1262, therefore, to suppress the noise components in the image 1268 and actualize the defect signal.

(Step S204)

The two sets of spatial filtering conditions that were determined in step S203 in order to obtain the lowest correlation are applied to the spatial filters 123a and 123b, and the inspection is conducted.

Second Embodiment

A second embodiment of an optical inspection device according to the present invention is described below using FIG. 9. The device configuration in the present embodiment is the same as the configuration described in the first embodiment shown in FIG. 1. The present embodiment differs from the first embodiment in that optical simulation is used during determination of spatial filtering conditions. Only the difference from the first embodiment is described here.

FIG. 9 is a flow diagram showing a process flow of spatial filtering condition setting with optical simulation. An image obtained by modeling a wafer surface region to be inspected, and applying spatial filters that filter out a diffraction pattern from the region to be inspected, is first derived (step S300). Next, average intensity T at the region to be inspected is calculated (step S301). Any value of the average intensity T or more is set as a threshold level "Tth", and a plurality of images are acquired under the spatial filtering conditions that assign intensity less than "Tth" to the region to be inspected (step S302). Two of the acquired number (n) of images are selected and an integrated processing calculation is performed on an "nC2" number of combinations (step S303). The combination of images having the lowest noise level is selected (step S304). The spatial filter shape corresponding to the calculation of the image combination which was determined in step S304 is assigned to the spatial filters 123a and 123b and the inspection is conducted (step S305).

Next, details of each step are described below.

(Step S300)

In step S300, the region to be inspected is modeled, the amount of light reflected, refracted, and scattered from the region, obtained on the pupil plane, is calculated by optical simulation, the spatial filters are applied, and the images acquired by the line sensors are calculated. The spatial filters are set to block all light diffracted from the patterns to be inspected, the setting method being substantially the same as the method of spatial filter setting in any one of the conventional techniques described in Patent Documents 1, 2. During the inspections using the conventional methods, the diffracted light is all blocked according to the assigned spatial filter conditions, but under these conditions, not only the pattern-diffracted light but also the defect signal itself are blocked.

(Step S301)

In step S301, the average intensity T at the target region from which the diffracted light was filtered out by the spatial filters is calculated from the images that were calculated, as images to be acquired by the line sensors, under the spatial filtering conditions set in step S300.

(Step S302)

In step S302, the average intensity T at the target region that was calculated in step S301 after spatial filtering has been applied is multiplied by a coefficient α, the "Tth" value expressed in terms of "Tth=Txa" is set as a threshold level, and the intensity at the region to be inspected is measured using the set "n" number of combinations of spatial filtering conditions that yield intensity values less than the threshold level. The coefficient α is set to obtain a defect detection signal permitting a certain degree of diffracted light leakage. At this time, if too great an α value is assigned, the defect signal will be buried in noise components, so α is set to be, for example, nearly 1.1 to detect microscopic defects equivalent to the average intensity T.

(Step S303)

In step S303, two combinations are selected from the "n" number of combinations of spatial filtering conditions that were determined in step S302, and integrated processing follows. In the integrated processing, for example, images based on weighted addition, multiplication, or the like are used.

(Step S304)

In step S304, the average intensity at the target region on the image obtained as a result of integrated processing of the "nC2" number of combinations that was calculated in step S303, is calculated and the combination having the smallest value is selected.
(Step S305)
The spatial filter shape corresponding to the calculation of the image combination which was determined in step S304 is assigned to the spatial filters 123a and 123b and the inspection is conducted.

Third Embodiment

A third embodiment of an optical inspection device according to the present invention is described below using FIGS. 10 and 11. FIG. 10 is a block diagram schematically showing the optical inspection device configuration according to the third embodiment of the present invention, and FIG. 11 is a block diagram schematically showing an image-processing unit configuration of the optical inspection device according to the third embodiment of the present invention.

The configuration of the present embodiment includes oblique detection optical systems 120c and 120d in addition to the configuration of the first embodiment that is shown in FIG. 1. In other words, an illumination optical system 110, detection optical systems 120a and 120b, a height detection unit 160, and a stage unit 170, all of which are shown in FIG. 10, are composed of the same elements as those described in the first embodiment per FIG. 1. In the third embodiment, by adding the oblique detection optical systems 120c and 120d, it makes possible to detect defect signals which are not detected by the detection optical systems (upward detection optical systems) 120a and 120b for detecting upward reflected, scattered, and diffracted light. This leads to the number of detectible defect kinds increasing and to defect detection sensitivity improving as well.

As with the upward detection optical systems 120a and 120b described in the first embodiment using FIG. 1, the oblique detection optical systems 120c and 120d include an objective lens 121c, spatial filters 123c and 123d, polarization state analyzers 124c and 124d, an imaging lens 125c, and line sensors 126c and 126d. A beam splitter 122c between the objective lens 121c and spatial filter 123c present in an optical path splits the optical path. The light passing through the beam splitter 122c forms an optical path leading to the oblique detection optical system 120c, and light reflected by the beam splitter 122c forms an optical path leading to the oblique detection optical system 120d. Positions and shapes of the spatial filters 123c and 123d differ from each other, as with those of the spatial filters 123a and 123b in the upward detection optical systems. In addition, although omitted in the configuration shown in FIG. 10, pupil observing optics 128a and 128b equivalent to those described in the first embodiment are provided in the optical paths of the upward detection optical systems 120a and 120b. Pupil observing optics equivalent to the pupil observing optics 128a and 128b are also provided in the optical paths of the oblique detection optical systems 120c and 120d.

A signal processing and control system 1250 includes an image processing unit 1200, an operating unit 1210, a control unit 1220, a display unit 1230, and a height detection unit 160.

The image processing unit 1200 produces images 1261 and 1262 of scattered light from a digital signal formed by amplification in A/D converters 129a and 129b following completion of detection in line sensors 126a and 126b, and from another digital signal formed by amplification in A/D converters 129c and 129d following completion of detection in line sensors 126c and 126d. The image processing unit 1200 also processes the produced images 1261 and 1262 of the scattered light from the semiconductor wafer 100 and extracts surface defects.

FIG. 11 is a block diagram schematically showing a configuration of the image processing unit 1200 in the third embodiment of the optical inspection device according to the present invention. The image processing unit 1200, which is substantially the same configuration as that of the image processing unit 200 described in the first embodiment using FIG. 2, includes a position matching element 2001a, a brightness corrector 2002a, an integration processor 2003a, and a defect analyzer 2004a, as elements that process the images generated from the signals which the detection optical systems 120a and 120b have detected. The image processing unit 1200 further includes a position matching element 2001c, a brightness corrector 2002c, an integration processor 2003c, and a defect analyzer 2004c, as elements that process the image 1263 generated from the scattered light which the detection optical system 120c has detected, and the image 1264 generated from the scattered light which the detection optical system 120d has detected. The image processing unit 1200 additionally includes a defect analytical result integrator 2006 that integrates analytical results received from the defect analyzers 2004 and 2004c, and a defect classifier/sizer 2005 that uses the integrated analytical results to classify and size defects. Since microscopic defects scatter a beam in diverse directions, the upward detection optical systems 120a and 120b and the oblique detection optical systems 120c and 120d are provided to detect two directions of light. In addition to enhancing a defect capture ratio, these detection systems enable defect classifying/sizing accuracy to be raised by conducting comparisons between intensity signals of the defects detected by the upward detection optical systems 120a and 120b, and intensity signals of the defects detected by the oblique detection optical systems 120c and 120d.

It has been described in the third embodiment above that the configuration of the image processing unit 1200 applies by analogy to the configuration described in FIG. 2 of the first embodiment. Alternatively, however, the configuration of the image-processing unit 1200 may apply by analogy to the configuration described in FIG. 3 or 4 of the first embodiment.

Fourth Embodiment

A fourth embodiment of an optical inspection device according to the present invention is described below using FIG. 12. The present embodiment differs from the third embodiment in that optical systems do not include a branch of an optical path in upward detection systems and oblique detection systems. The present invention aims at suppressing noise due to wafer surface patterns, by adopting different methods for setting spatial filters 123a and 123c. In the configuration of the present embodiment, therefore, in preparing a recipe and/or in conducting an inspection, two sets of spatial filtering conditions are assigned in each of the detection systems 120a and 120c and the inspection is repeated twice, whereby images similar to those obtained in the third embodiment are acquired. The method of processing the acquired images is the same as in the third embodiment, so description of the processing method is omitted.

While details of the invention by the present inventors have been described above on the basis of the embodiments, the invention is not limited thereto and may obviously incorporate various changes and modifications without departing from the scope of the invention.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

DESCRIPTION OF REFERENCE NUMBERS

100 . . . Semiconductor wafer
101 . . . Linear beam
110 . . . Illumination optical system
111 . . . Laser light source
112 . . . ND filter
113 . . . Beam expander
114 . . . polarization state generator
115 . . . Linear beam generator
120a, 120b, 120c, 120d . . . Detection optical systems
121, 121c . . . Objective lenses
122, 122c . . . Beam splitters
123a, 123b, 123c, 123d . . . Spatial filers
124a, 124b, 124c, 124d . . . polarization state analyzers
126a, 126b, 126c, 126d . . . Line sensors
127a, 127b . . . Beam samplers
128a, 128b . . . Pupil plane-observing optics
1261, 1262, 1264, 1265 . . . Acquired images
1268, 1269 . . . Integrated images
160 . . . Height detection unit
161 . . . Light transmitter
170 . . . Stage unit
170a . . . x-stage
170b . . . y-stage
170c . . . z-stage
170d . . . θ-stage
200, 1200 . . . Image processing units
210, 1210 . . . Operating units
220, 1220 . . . Control units
230, 1230 . . . Display units
250, 1250 . . . Signal processing and control systems
2001, 2011a, 2011b, 2021a, 2021b, 2001c . . . Position-matching elements
2002, 2012a, 2012b, 2022a, 2022b, 2002c . . . Brightness correctors
2003, 2003a, 2003c . . . Integration processors
2013a, 2013b, 2023a, 2023b . . . Differential processors
2004, 2014, 2004a, 2004c . . . Defect analyzers
2028, 2006 . . . Defect analytical result integrators
2005, 2005c, 2029 . . . Defect classifier/sizer.

The invention claimed is:

1. A defect inspection device comprising:
illumination unit that irradiates an object to be inspected, with light, the object having patterns formed on a surface;
light collecting unit that collects light reflected, diffracted, and scattered from the object irradiated with the light by the illumination unit;
optical path branching unit that branches the light collected by the light collecting unit upon receiving the light reflected, diffracted, and scattered from the object into a first detection optical path and a second detection optical path;
a first spatial filter fitted with a first light blocking pattern to block specific reflected, diffracted, and scattered light of the reflected, diffracted, and scattered light traveling towards the first detection optical path created as a result of branching by the optical path branching unit;
first imaging unit that forms an image from the light passed through the first spatial filter;
first image acquisition unit that acquires a first image by detecting the image formed by the first imaging unit;
a second spatial filter fitted with a second light blocking pattern different from the first light blocking pattern, to block specific reflected, diffracted, and scattered light of the reflected, diffracted, and scattered light traveling towards the second detection optical path created as a result of branching by the optical path branching unit;
second imaging unit that forms an image from the light passed through the second spatial filter;
second image acquisition unit that acquires a second image by detecting the image formed by the second imaging unit; and
image processing unit that conducts image processing to extract defect candidates by integratedly processing the first image acquired by the first image acquisition unit and the second image acquired by the second image acquisition unit.

2. The defect inspection device according to claim 1, wherein the illumination unit irradiates the object with linear shaped light in a direction inclined with respect to a direction normal to the object.

3. The defect inspection device according to claim 1, wherein the light collecting unit collects, of the light reflected, diffracted, and scattered from the object which the illumination unit has irradiated with light, the light reflected, diffracted, and scattered in a direction normal to the object.

4. The defect inspection device according to claim 1, further comprising, in the first detection optical path and the second detection optical path, a polarizing element formed to control a polarization state.

5. A defect inspection method comprising the steps of:
irradiating an object to be inspected, with light, the object having patterns formed on a surface;
collecting light reflected, diffracted, and scattered from the object irradiated with the light;
branching the collected light of the light reflected, diffracted, and scattered from the object into a first detection optical path and a second detection optical path;
blocking, via a first spatial filter fitted with a first light blocking pattern, specific reflected, diffracted, and scattered light among the reflected, diffracted, and scattered light traveling towards the first detection optical path created as a result of branching;
forming a first optical image from the light passed through the first spatial filter;
acquiring a first image by detecting the formed first optical image with a first detector;
blocking, via a second spatial filter fitted with a second light blocking pattern different from the first light blocking pattern, specific reflected, diffracted, and scattered light among the reflected, diffracted, and scattered light traveling towards the second detection optical path created as a result of branching;
forming a second optical image from the light passed through the second spatial filter;
acquiring a second image by detecting the formed second optical image with a second detector; and
determining defect candidates by integratedly processing the acquired first image and second image.

6. The defect inspection method according to claim 5,
wherein, in the step of irradiation with light, the object to be inspected is irradiated with linear shaped light in a direction inclined with respect to a direction normal to the object.

7. The defect inspection method according to claim 5,
wherein, of the light reflected, diffracted, and scattered from the object which has been irradiated with light, the light reflected, diffracted, and scattered in a direction normal to the object is collected.

8. The defect inspection method according to claim 5,
wherein the reflected, diffracted, and scattered light traveling towards the first detection optical path or the second detection optical path is subjected to control of a polarization state.

9. A defect inspection method comprising:
irradiating an object to be inspected, with light, the object having patterns formed on a surface;
collecting light reflected, diffracted, and scattered from the object irradiated with the light, then detecting with a first detector a first optical image formed by a light passed through a first spatial filter fitted with a first light blocking pattern, and thus acquiring a first image;
collecting light reflected, diffracted, and scattered from the object irradiated with the light, then detecting with a second detector a second optical image formed by a light passed through a second spatial filter fitted with a second light blocking pattern, and thus acquiring a second image; and
determining defect candidates by integratedly processing the acquired first image and second image.

10. The defect inspection method according to claim 9,
wherein the first image is an image obtained upon the first detector detecting the first optical image formed by a light guided to a first optical path by optical path branching unit upon the collection of the reflected, diffracted, and scattered light, and the second image is an image obtained upon the second detector detecting the second optical image formed by a light guided to a second optical path by the optical path branching unit upon the collection of the reflected, diffracted, and scattered light.

11. The defect inspection method according to claim 9,
wherein the first image is an image obtained upon the first detector detecting the first optical image formed by collecting, of the light reflected, diffracted, and scattered from the object, the light heading in a perpendicular direction relative to, and towards a neighborhood of, the object to be inspected, and the second image is an image obtained upon the second detector detecting the second optical image formed by collecting, of the light reflected, diffracted, and scattered from the object to be inspected, the light heading in an oblique direction relative to the object to be inspected.

* * * * *